(12) United States Patent
Paoletti et al.

(10) Patent No.: US 9,932,416 B2
(45) Date of Patent: Apr. 3, 2018

(54) ENAMEL-DENTIN ADHESIVES BASED ON CHEMICALLY MODIFIED NATURAL POLYSACCHARIDES

(71) Applicant: Universita' Degli Studi Di Trieste, Trieste (IT)

(72) Inventors: Sergio Paoletti, Trieste (IT); Roberto Di Lenarda, Trieste (IT); Lorenzo Breschi, Pianoro (IT); Milena Cadenaro, Trieste (IT); Marina Diolosa', Trieste (IT); Gianluca Turco, Trieste (IT); Ivan Donati, Sedegliano (IT)

(73) Assignee: Universita' Degli Studi Di Trieste, Trieste (IT)

( * ) Notice: Subject to any disclaimer, the term of this patent is extended or adjusted under 35 U.S.C. 154(b) by 45 days.

(21) Appl. No.: 15/121,504

(22) PCT Filed: Feb. 26, 2015

(86) PCT No.: PCT/EP2015/054014
§ 371 (c)(1),
(2) Date: Aug. 25, 2016

(87) PCT Pub. No.: WO2015/128415
PCT Pub. Date: Sep. 3, 2015

(65) Prior Publication Data
US 2016/0362503 A1  Dec. 15, 2016

(30) Foreign Application Priority Data

Feb. 27, 2014 (IT) .............. PD2014A0043

(51) Int. Cl.
*A61L 24/08* (2006.01)
*A61K 6/097* (2006.01)
*C08B 37/08* (2006.01)
*A61K 6/083* (2006.01)

(52) U.S. Cl.
CPC ............ *C08B 37/003* (2013.01); *A61K 6/083* (2013.01); *A61K 6/097* (2013.01); *A61L 24/08* (2013.01)

(58) Field of Classification Search
CPC ........ C08B 37/003; A61K 9/097; A61K 24/08
See application file for complete search history.

(56) References Cited

U.S. PATENT DOCUMENTS

| 2005/0074415 | A1 | 4/2005 | Chow |
| 2007/0031467 | A1* | 2/2007 | Abrahams ............. A61L 24/043 424/423 |
| 2007/0092580 | A1 | 4/2007 | Chow et al. |
| 2009/0238875 | A1* | 9/2009 | Noh ...................... C08B 37/003 424/487 |
| 2011/0182995 | A1 | 7/2011 | Asgary |
| 2012/0178684 | A1 | 7/2012 | Liu et al. |

FOREIGN PATENT DOCUMENTS

| EP | 0323632 | 7/1989 |
| EP | 0329098 | 8/1989 |
| WO | WO2007083870 | 7/2007 |
| WO | WO2009029734 | 3/2009 |
| WO | WO2009029049 | 5/2009 |
| WO | WO2012009555 | 1/2012 |

OTHER PUBLICATIONS

Brian G. Amsden, Abby Sukarto, Darryl K. Knight and Stephen N. Shapka; "Methacrylated Glycol Chitosan as a Photopolymerizable Biomaterial"; Biomacromolecules; 2007; pp. 3758-3766.
I.M. El-Sherbiny, R.J. Lins, E.M. Abdel-Bary and D.R.K. Harding; "Preparation, Characterization, Swelling and In Vitro Drug Release Behaviour of Poly{N-acryloylglycine-chitosan] Interpolymeric pH and Thermally-Responsive Hydrogels"; European Polymer Journal; Jul. 2005; pp. 2584-2591.
Manoj Pati and P.L. Nayak; "Graft Copolymerization of Methyl Acrylate on Chitosan: Initiated by Ceric Ammonium Nitrate as the Initiator-Characterization and Antimicrobial Activity"; Pelagia Research Library; 2002; pp. 1646-1654.

* cited by examiner

*Primary Examiner* — Leigh C Maier
(74) *Attorney, Agent, or Firm* — Stetina Brunda Garred & Brucker

(57) ABSTRACT

The present invention concerns the preparation of chemically modified derivatives of chitosan with acrylic groups and their use in the field of enamel-dentin adhesives. Chitosan derivatives have physical-chemical features (hydrophilicity, presence of electrical charges on the chain) which allow them to interact with the organic part of the demineralized tooth. At the same time, the acrylic groups incorporated in the polymer chain allow the formation of a covalent bond with the restorative material used in the dental field that is typically composed of acrylic resins. By combining the adhesion to the tooth surface and the bond with the restorative material, the chemically modified chitosan described herein is able to increase the lifespan of the dental restoration and can thus find use in the field of adhesives, in particular enamel-dentin adhesives.

16 Claims, 4 Drawing Sheets

ENAMEL-DENTIN ADHESIVES BASED ON CHEMICALLY MODIFIED NATURAL POLYSACCHARIDES

CROSS REFERENCE TO RELATED APPLICATIONS

The present application claims priority to PCT International Application No. PCT/EP2015/054014 filed on Feb. 26, 2015, which application claims priority to Italian Patent Application No. PD2014A000043 filed Feb. 27, 2014, the entirety of the disclosures of which are expressly incorporated herein by reference.

STATEMENT RE: FEDERALLY SPONSORED RESEARCH/DEVELOPMENT

Not Applicable.

FIELD OF THE INVENTION

The invention relates to a chitosan chemically modified with the introduction of covalently bonded acrylic groups, the use thereof for preparation of adhesive compositions, in particular for enamel-dentin adhesive compositions.

STATE OF THE ART

The development of appropriate enamel-dentin adhesive systems in the field of dental restorations is a very important and broadly developed application sector. Dental caries are historically considered the main disease among the diseases of the oral cavity, representing the most common disease in most high-income countries, where this disease affects approximately 60-90% of school children and almost 100% of the adult population in most countries. The consequences of caries can be pain, tooth and oral function loss. Caries, affecting the aesthetics of the smile, can also have psychological and behavioral effects on the patient, thus resulting in a reduced quality of life. In addition, some of its effects, such as dental abscesses, are risk factors or cause of many systemic diseases, even potentially fatal. The modern caries therapy consists in its complete removal and subsequent application of a restoration to restore the correct morphology and function of the dental element. The creation of effective and long-lasting dental restorations is essential since this allows reducing the long-term cost of the dental treatment and improving the quality of life of patients.

Currently, the adhesive systems and composite resins, in particular acrylic-based, are the most used materials for dental restorations. The main reasons for which conservative treatments are carried out using acrylic-based composite materials and adhesive systems are: primary caries, secondary caries, tooth fracture and other causes, including fractures/infiltration of the margin or loss of previous restoration or loss of tooth substance related to the endodontic cavity accession. The longevity of the dental restoration depends on many factors, including the characteristics of the materials used, the level of oral hygiene and the patient's type of diet and the manual skills of the dentist.

The adhesive systems interact with the enamel-dentin tissue, at the level of the outermost layer of such tissues and on the cutting debris constituting the smear layer produced by the mechanical instruments (mechanical or manual) used for the removal of caries, through two adhesion strategies: "etch & rinse" and "self-etch" (Breschi L. et al., *Dental Mater.*, 2008, 24, 90-101). Currently, the classification of different adhesive systems is made according to the number of steps required for proper application (Van Meerbeek B. et al., *Operating Dent.*, 2003, 28, 215-235). The impregnation by the adhesive systems of the surface of the tooth tissue causes the formation of the hybrid layer, due to the interaction between the adhesive system and the substrate demineralized by the etching treatment. The stability over time of the restoration depends on the formation of a stable and homogeneous hybrid layer.

Typically, the average length of a restoration carried out using composite resins is about six years (Bohaty B. S. et al., *Clin. Cosmet. Investig. Dent*, 2013, 5, 33-42). The possibility of increasing the average length of a dental restoration would certainly have a positive impact on the treatment of secondary dental caries and the subsequent reconstruction of the restoration. This last statement is supported by the fact that both researchers and dental material industries are constantly looking for more effective and lasting, more easily manipulated and applicable materials and for this reason, often the manufacturers tend to vary the composition of adhesive systems and composite resins.

For many applications in the biomedical field, polysaccharide-based systems are particularly interesting. Generally, these polymers are highly biocompatible; as such, they are ideal for applications involving the direct contact with biological tissues.

Among the polysaccharides of natural origin, chitosan is one of the most studied and commercially used. This is a basic polysaccharide, of molecular weight between 20 and 1,500 kDa, consisting of a chain of residues of D-glucosamine ($GlcNH_2$) bonded by β1→4 bonds with interspersed units of N-acetyl-glucosamine (GlcNAc) and usually the "degree of acetylation" or "residual acetylation" (i.e., the percentage of GlcNAc units on the sum of $GlcNH_2$ and GlcNAc units) determines the features of chitosan together with the molecular weight. It is a cationic polysaccharide normally insoluble in neutral or basic aqueous solutions; in acidic solutions with a pH≤6.5, the free amino group is protonated making the polymer soluble. This polymer is already widely used in the biomedical field as it shows a low immune, pathological or infectious response (Suh Francis J. K., Matthew H. W. T. *Biomaterials*, 2000, 21, 2589-2598; Miyazaki S. et al. *Chem. Pharm. Bull.*, 1981, 29, 3067-3069). In particular, it is not cytotoxic, thus it is highly biocompatible with cells and biological tissues. Chitosan further has chemical-physical properties ideal for use as a biomaterial, such as the high density of cationic charge in acidic solution and the high processability, thanks to which it is possible to obtain porous structures on which cell cultures can be easily cultivated. Furthermore, the high hydrophilicity of the polysaccharide allows the interaction thereof with other biological macromolecular structures present in tissues, such as collagen and glycosaminoglycans.

Many recent studies have focused on the development of methodologies to enhance the biological effects of chitosan. In particular, most of the efforts have been aimed at increasing the cationic charge of the polymer or at modifying the chemical and bioavailability features thereof through (bio) chemical modifications. It is actually in its derivatized forms that chitosan takes the necessary properties for use as a biomaterial.

The use of chitosan as such or its derivatives in compositions usable as filler materials for orthopedic and dental applications has long been known.

Patents EP0323632 and EP0329098 disclose the use of acidic solutions of chitosan in combination with hydroxyapatite and with other metal oxides, such as zinc and/or magnesium oxide, as reinforcement in the production of hardening filler materials for applications in the orthopedic and dental fields.

Likewise, patent application US2005/0074415 describes the use of chitosan and derivatives thereof, such as non-toxic gelling agents in the preparation of a formulation based on calcium phosphate for the dental restoration and for implants and bone restoration. The role of gelling agents, including chitosan and its derivatives, is to increase the cohesiveness of the restoration paste. There are, however, no specific references to the type of chitosan derivatives that are proposed.

Patent application US2007/0092580 describes the use of chitosan and biocompatible derivatives thereof, in particular malate and lactate chitosan, as compounds forming hydrogels usable in the preparation of a dual-phase cement precursor. In this specific use, the formation of the chitosan hydrogel and of biocompatible derivatives thereof occurs following the treatment of the system with a strong base, e.g. sodium hydroxide.

Patent application WO2009/029049 describes the use of unsaturated derivatives of chitin and chitosan, and in particular of chitin-methacrylate and chitosan itaconate, as tixotropic agents in a composition usable as a bone and/or dental cement and as bone filler.

Patent application WO2009/029734 discloses the use of chitin and chitosan as a filler in a cement for the treatment of bone defects in dental or orthopedic applications composed of a polymerizable resin comprising ethylene unsaturated bonds, a glycidyl ether and/or isocyanate group and primary, secondary, tertiary or quaternary amines.

Patent application US2011/0182995 describes calcium-based cements usable as dental or orthopedic fillers, which includes the use of synthetic and natural polymers, including chitosan, as biodegradable and absorbable materials.

Patent application US2012/0178684 describes the use of chitosan as a biocompatible filler material for surgical bone cements for applications in the orthopedics, dental, maxillofacial surgery fields.

Patent application WO2012/009555 describes the use of chitosan as an additional filler in the preparation of a polymeric composite for dental restoration containing a polymeric matrix and a reinforcing filler in the form of nanofibers, nanoplates and submicrometric fibers or plates.

The use of chitosan in dentistry is booming even as adhesive. Recently, Elsaka et al. (Elsaka S. E. *Quintessence Int.*, 2012, 43, 603-613) have proposed the use of non-modified chitosan as an additive to the "self-etch" adhesive system RealSeal®. However, despite the antibacterial properties due to the presence of chitosan, the adhesive system containing the polysaccharide showed no significant difference in the strength of the bond with the restoration as compared to the same system without non-modified chitosan.

SUMMARY

A first purpose of the present invention is the preparation of a covalently derivatized chitosan, so as to obtain a compound which is able to interact with both the organic component of the demineralized dentin (mainly collagen) and with the monomers composing the restoration resin.

A second purpose of the present invention is the use of a derivatized chitosan having suitable features (molecular weight of the polymer, degree of derivatization) within an enamel-dentine adhesive composition in order to significantly increase the average lifetime of the dental restoration.

The increase of the adhesive strength of adhesive systems, which include the chemically modified chitosan, may find useful application, besides the dental field, also in the orthopedic and ophthalmic fields.

A further purpose of the present invention therefore is the use of a derivatized chitosan for the development of adhesives also usable in the orthopedic and ophthalmic fields. In order to achieve the above purposes, the inventors have developed appropriate water soluble polysaccharide systems based on a modified chitosan able to produce effective adhesive compositions and to guarantee a longer duration of the dental restoration. Such adhesive compositions are characterized in that the usual resins used for the purpose are admixed with a chitosan modified by covalent derivatization with acrylic units.

Therefore, in a first aspect the object of the invention is a chitosan modified by derivatization of residues —$NH_2$ of D-Glucosamine units, which can be schematically represented by the general formula I

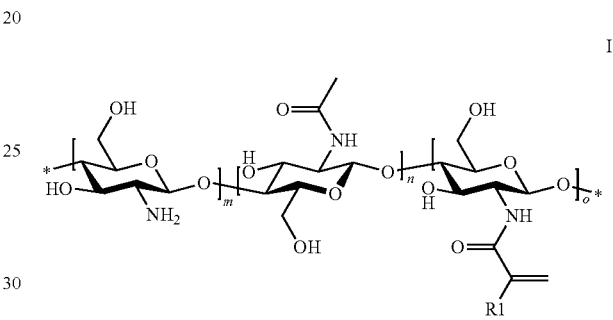

wherein:
the chitosan has a degree of total substitution of D-Glucosamine units with CO—$C(CH_2)R_1$ acrylic and acetyl residues comprised from 10% to 50% with a ratio between acrylic and acetyl residues comprised from 0.1 to 9; and $R_1$ is selected from H, a halogen, a linear or branched $C_1$-$C_3$ alkyl chain, optionally substituted with an OH or a halogen, and $NHCOR_2$ with $R_2$ equal to a linear or branched $C_1$-$C_3$ alkyl chain.

In another aspect, the object of the invention is the use of the chitosan chemically modified by derivatization of —$NH_2$ residues of the D-glucosamine of general formula I as a conditioner for the preparation of adhesive systems usable in the dentistry, orthopedic and ophthalmic fields.

Yet in a further aspect, the object of the invention is a composition with adhesive properties comprising at least one chitosan chemically modified by derivatization of the —$NH_2$ residue of D-glucosamine according to the general formula I in combination with appropriate additives and excipients.

The objects and the advantages of the use of the chitosan modified with acrylic groups within adhesive compositions object of the present invention will be better understood in the course of the following detailed description where, by way of a non-limiting example of the invention, some examples of preparation of chitosan derivatives with acrylic groups, their use in combination with adhesive systems, their physical-chemical characterization as well as the mechanical tests for the evaluation of their properties will be described.

DETAILED DESCRIPTION OF THE INVENTION

Figure 1:
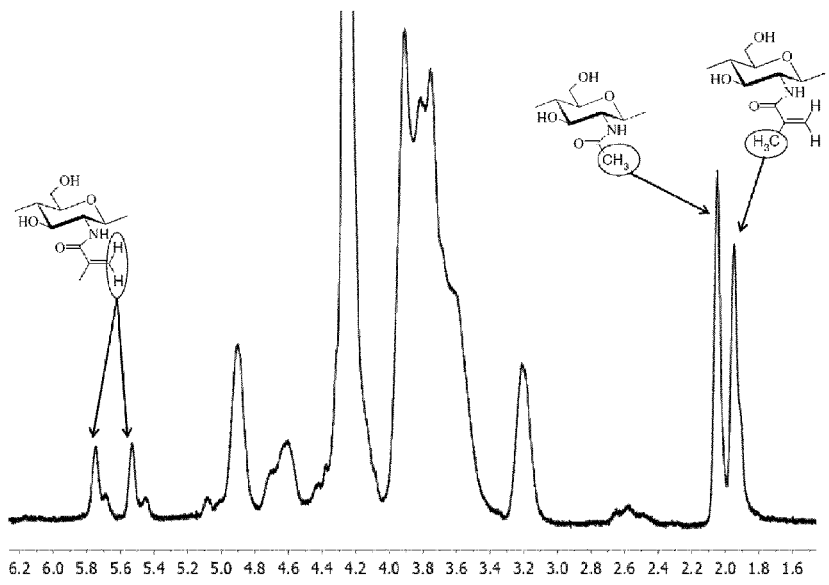
FIG. 1. $^1$H-NMR of the chitosan modified with methacrylic acid prepared according to example 1.

The main purpose of the present invention is the development of a chitosan having chemical features adapted to be used in compositions used as adhesive systems in the first place in the dental field but also in other biomedical fields, such as the orthopedic and the ophthalmic field.

For the purposes of the present invention, the chemically modified chitosan is derivatized on residues —$NH_2$ of D-glucosamine and can be schematically represented by the general formula I

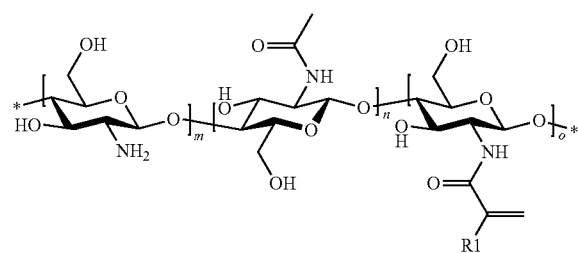

I wherein;
the chitosan has a degree of total substitution of the D-Glucosamine units with CO—C($CH_2$)$R_1$ acrylic and acetyl residues between 10% and 50% with a ratio between acrylic and acetyl residues comprised from 0.1 to 9; and $R_1$ is selected from H, a halogen, a linear or branched $C_1$-$C_3$ alkyl chain, optionally substituted with an OH or a halogen, and $NHCOR_2$ with $R_2$ equal to a linear or branched $C_1$-$C_3$ alkyl chain.

The representation given hereinabove for the chemically modified chitosan derivatives, object of the invention, is a schematic representation since the D-Glucosamine units bearing covalently linked acetyl or acrylic residues are interdispersed in the polymeric chain of chitosan as one skilled in the art can easily understood.

Since the acrylic residue of the chemically modified chitosan derivatives, object of the invention, is the initiator residue of the polymerization of the resin used for restoration, the —CO—C($CH_2$)$R_1$ group can be an acrylic or methacrylic residue commonly used for these purposes and preferably, $R_1$ is selected from H, $CH_3$, $CH_2CH_3$, $CH_2CH_2CH_3$, $CH_2CH_2OH$, Br, $CH_2Br$ and $NHCOCH_3$.

On the other hand, the chitosan component in covalent derivatives herein disclosed is the portion that gives adhesive properties to the same and that at the same time ensures an optimal dispersion of the same in the resins used so as to give rise to a stable nano-composite material with a viscosity suitable for use.

To this end, the physical-chemical features (hydrophilicity, presence of electrical charges on the chain) of chitosan, which allow the derivatives themselves to interact with the organic part of the demineralized tooth, are essential. In particular, in order to ensure the adhesion to the demineralized tooth, the modified chitosan keeps a certain number of residues —$NH_2$ of D-Glucosamine free to interact with the components of dentine. Additionally the aqueous solubility of chitosan derivatives with acrylic residues of general formula I object of the invention is crucial for a miscibility of the same in adhesive systems. In this sense, in the modified chitosan, the fraction of D-Glucosamine units bearing acetyl groups (D-N-acetyl-Glucosamine) and acrylic groups (D-N-acrylic-Glucosamine) does not exceed 50%. Preferably, the ratio between D-Glucosamine units substituted with acrylic groups D-N-acrylic-Glucosamine and N-acetyl-D-Glucosamine units is between 0.1 and 9 and more preferably, this ratio is 1 (1:1). Preferably, the chitosan in covalent derivatives of general formula I object of the invention has a residual acetylation degree between 5 and 20% and more preferably, of 16% and a degree of substitution with acrylic residues between 5 and 24% and more preferably, of 16%.

The molecular weight (hereafter indicated with MW) of the chitosan polymer which can be used to obtain said acrylic derivatives can reach up to 400,000 Da (conventionally: 400 kDa) and preferably is in the range from 20 kDa to 300 kDa and more preferably, in the range from 40 kDa to 100 kDa. The molecular weight of the starting chitosan is a substantial functional parameter since it determines the viscosity of the aqueous solution containing it. In fact, the enamel-dentin adhesive comprising the chitosan substituted with acrylic groups on the —$NH_2$ residues of D-Glucosamine units according to the invention must have a sufficient fluidity to penetrate inside the dentinal porosities, which are formed as a result of the acid treatment that the tooth undergoes before restoration. Moreover, a suitable viscosity allows for the impregnation of the collagen fibrils exposed and the consequent formation of a suitable hybrid layer. Proof of this is the fact that the use of a chitosan modified with acrylic groups with a molecular weight of 600 kDa within the system does not lead to any advantage in terms of duration of the restoration over time. At the same time, a too low molecular weight does not allow the onset of a suitable number of effective electrostatic interactions between the chitosan modified with acrylic groups and the organic components (mainly collagen and glycosaminoglycans) present on the demineralized dentin. In fact, this number depends on the amount of free amino groups per chain of modified chitosan, and thus on the molecular weight and on the degree of substitution.

Therefore, the chitosan derivatives of general formula I according to the invention have proved to be effectively usable for the preparation of adhesive compositions useful to increase the average duration of a dental restoration based on the use of acrylic resins. For this use, a chitosan modified with acrylic groups of general formula I can be added to an adhesive composition containing a hydrophilic acrylic or methacrylic compound selected from, for example, hydroxyethyl acrylate (HEMA) or other acrylates used in known dental adhesives (Van Landuyt, K. L. et al. *Biomater,* 2007, 28, 3757-3785). HEMA is to be preferred since is a small hydrophilic monomer widely used in dentistry (Van Landuyt K. L. et al. *Dental Mater,* 2008, 24, 1412-1419. Hitmi L. et al., *Dent Mater,* 2002, 18, 503-511). The main feature of this monomer is its good biocompatibility when polymerized and HEMA is often added to formulations of adhesive systems to ensure good wettability of dentin. The structure of this monomer improves the stability of solutions containing hydrophobic and hydrophilic elements.

The minimum amount of the acrylic compound, to be combined with at least one of the chemically modified chitosan derivative of the present invention in the adhesive compositions, is of 10% (V/V). Preferably, the amount of the acrylic compound is comprised from at least 10% (V/V) and up to 30% (V/V) (Cadenaro M. et al. *Dent Mater* 2009; 25(5):621-28).

The amount of modified chitosan to be added to the adhesive system is less than 4% (w/V), preferably the concentration of chitosan modified with acrylic groups is between 0.2% and 2% (w/V) and most preferably it is 1% (w/V).

As experimentally tested, adding an unmodified chitosan to the adhesive system does not cause significant increases in the adhesion between the demineralized dentin and the resin restoration material after incubation in artificial saliva for 24 hours. Unexpectedly, however, the presence of a chitosan modified with acrylic groups causes greater adhesion strength of the restoration to dentin following a simulated aging process, indicating the ability of these chitosan derivatives to increase the average lifespan of the restoration.

For the chitosan modified with acrylic groups to be water soluble and miscible, the adhesive compositions have a percentage of an aqueous solution of not less (i.e. equal or higher) than 30% (V/V). Preferably, the percentage of the aqueous solution in the adhesive composition is in the range between 40% and 50% (V/V) and more preferably, this percentage is 50% (V/V). In addition, the aqueous solution is preferably acidic and has a pH between 1 and 6.5 and more preferably, the pH is 5.5.

Furthermore, the adhesive compositions comprising a modified chitosan of general formula I can further comprise hydroxyethyl methacrylate (HEMA).

For the pursued purposes, the aspects concerning the preparation and incorporation of a chitosan derivative with acrylic groups into an adhesive system have been addressed. According to the invention, these goals are bases on the exploitation of the ability of these chitosan derivatives to interact with dentin and, thanks to the presence of acrylic residues, to chemically bind with the resins composing the dental restoration.

The process of preparing such chitosan derivatives envisages the treatment of a chitosan solution in acidic environment (pH 5.5) with the acrylic groups containing a carboxylic acid in the presence of a condensing agent such as 1-ethyl-3-(3-dimethylaminopropyl)carbodiimide (EDC).

By way of a non-limiting example, the following is general description of the preparation of chitosans modified with acrylic groups and their use in water-based dental adhesives.

EXAMPLES

Example 1: Derivatization of Chitosan with Methacrylic Acid—1 Equivalent 13.2 g of chitosan (PM 70,000 Da; residual degree of acetylation 16%) were dissolved in 500 mL of a buffer of morpholinoethanesulfonic acid (MES) 0.05 M at pH 5.5. Methacrylic acid (660 µL) was added dropwise to the chitosan solution followed by N-hydroxysuccinimide (1.36 g) and ethyl-3-(3-dimethylaminopropyl)carbodiimide (EDC) (2.24 g). The solution was kept under stirring for 24 hours, dialyzed against a solution of $NaHCO_3$ (0.05 M), NaCl (0.1 M) and water. The solution was then lyophilized.

The resulting degree of substitution with methacrylic residues is of 16%.

Example 2: Derivatization of Chitosan with Acrylic Acid—1 Equivalent 0.30 g of chitosan (PM 70,000 Da; residual degree of acetylation 16%) were dissolved in 120 mL of a buffer of morpholinoethanesulfonic acid (MES) 0.05 M at pH 5.5. Acrylic acid (133 µL) was added dropwise to the chitosan solution followed by N-hydroxysuccinimide (0.34 g) and EDC (0.56 g). The solution was kept under stirring for 24 hours, dialyzed against a solution of $NaHCO_3$ (0.05 M), NaCl (0.1 M) and water. The solution was then lyophilized.

The resulting degree of substitution with acrylic residues is of 12%.

Example 3: Derivatization of Chitosan with 2-ethyl Acrylic Acid—1 Equivalent 0.30 g of chitosan (PM 70000 Da; residual degree of acetylation 16%) were dissolved in 120 mL of a buffer of morpholinoethanesulfonic acid (MES) 0.05 M at pH 5.5. 2-ethyl acrylic acid (198 µL) was added dropwise to the chitosan solution followed by N-hydroxysuccinimide (0.34 g) and EDC (0.56 g). The solution was kept under stirring for 24 hours, dialyzed against a solution of $NaHCO_3$ (0.05 M), NaCl (0.1 M) and water. The solution was then lyophilized.

The resulting degree of substitution with acrylic residues is of 13%.

Example 4: Derivatization of Chitosan with 2-bromo Acrylic Acid—1 Equivalent 300 mg of chitosan (PM 70000 Da; residual degree of acetylation 16%) were dissolved in 120 mL of a buffer of morpholinoethanesulfonic acid (MES) 0.05 M at pH 5.5. 2-bromo acrylic acid (0.294 g) was added dropwise to the chitosan solution followed by N-hydroxysuccinimide (0.34 g) and EDC (0.56 g). The solution was kept under stirring for 24 hours, dialyzed against a solution of $NaHCO_3$ (0.05 M), NaCl (0.1 M) and water. The solution was then lyophilized.

The resulting degree of substitution with acrylic residues is of 10%.

Example 5: Preparation of an Adhesive System Containing Chitosan Derivatized with Methacrylic Acid (1% w/V Final)

The chitosan modified with methacrylate groups described in example 1 (0.20 g) was dissolved in 10 mL of a buffer solution of morpholinoethanesulfonic acid (50 mM) at pH 5.5. 6 mL of hydroxyethyl methacrylate (HEMA) (final concentration 30% V/V) and 4 mL of ethanol were added to the solution. The final concentration of chitosan derivative in the adhesive system is of 1% (w/V).

Example 6: Preparation of an Adhesive System Containing Chitosan Derivatized with Acrylic Acid (1% w/V Final)

The chitosan modified with acrylate groups described in example 2 (0.20 g) was dissolved in 10 mL of a buffer solution of morpholinoethanesulfonic acid (50 mM) at pH 5.5. 6 mL of hydroxyethyl methacrylate (HEMA) (final concentration 30% V/V) and 4 mL of ethanol were added to the solution. The final concentration of chitosan derivative in the adhesive system is of 1% (w/V).

Example 7: Preparation of an Adhesive System Containing Chitosan Derivatized with Methacrylic Acid (2% w/V Final)

The chitosan modified with methacrylate groups described in example 1 (0.40 g) was dissolved in 10 mL of a buffer solution of morpholinoethanesulfonic acid (50 mM) at pH 5.5. 6 mL of hydroxyethyl methacrylate (HEMA) (final concentration 30% V/V) and 4 mL of ethanol were added to the solution. The final concentration of chitosan derivative in the adhesive system is of 2% (w/V).

Example 8: Preparation of an Adhesive System Containing Chitosan Derivatized with Methacrylic Acid (0.5% w/V Final)

The chitosan modified with methacrylate groups described in example 1 (0.10 g) was dissolved in 10 mL of a buffer solution of morpholinoethanesulfonic acid (50 mM) at pH 5.5. 6 mL of hydroxyethyl methacrylate (HEMA) (final concentration 30% V/V) and 4 mL of ethanol were added to the solution. The final concentration of chitosan in the adhesive system is of 0.5% (w/V).

Example 9: Preparation of Resin R2

The experimental resin R2 (consisting of BisGMA 70% by weight; TEGDMA 28% by weight EDMAB 0.5% by weight; TPO 0.5% by weight CQ 0.25% by weight) was used as an adhesive since it has hydrophobic properties similar to those present in the commercial "etch & rinse" adhesives. The choice of a hydrophobic resin is supported by the fact that such resins tend to form bonds with the dentine with a high level of adhesion (Nishitani Y. et al, *J Dent Res*, 2006, 85, 1016-1021). The resin R2 was prepared according to the article by Cadenaro et al. (Cadenaro M. et al, *Dent Mater,* 2009, 25, 1269-1274). In this study, however, the resin was modified by introducing a second photo-initiator agent: TPO (2,4,6-trimethylbenzoyl-diphenylphosphine oxide) to allow the use of the adhesive system with different types of photo-polymerization lamps available on the market.

As an example, the physical and chemical features of the chitosan modified with methacrylic groups of example 1 and its use within a water-based adhesive system are hereafter reported. Similar results were obtained with all the exemplified acrylic derivatives, object of the present invention, herein disclosed.

Example 10: Characterization of the Chitosan Modified with Acrylic Residues and of its Incorporation in the Adhesive System The chemical reaction between chitosan and acrylic units that have a carboxylic acid, as described in the previous examples 1-4, leads to the formation of amide bonds between the polymer and the acrylic monomers. The presence of the latter was verified through $^1$H-NMR spectroscopy, which clearly shows the signals due to the acrylic group, specifically to the methacrylic residues introduced on the chain according to example 1 (FIG. 1).

Figure 2:
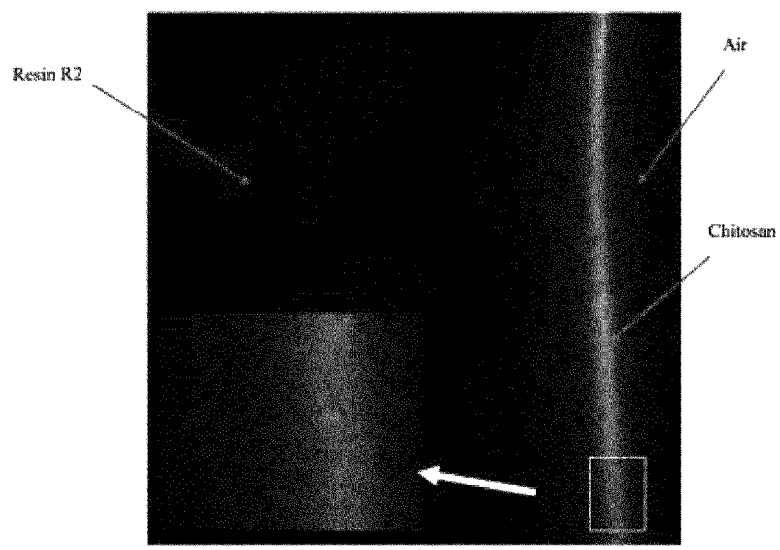
FIG. 2. 20× image obtained by Confocal Laser Scanning Microscope (CLSM) of the interface surface between the adhesive and the resin in a parallelepiped. The light stripe corresponds to the marked methacrylated chitosan while on the left there is the resin and on the right there is air, both being non-fluorescent.

The presence of the acrylic residues on the chitosan chain allows the crosslinking of the latter with the acrylic monomers present in the composite used for restoration. This is visible in FIG. 2 where, thanks to the use of a chitosan modified with methacrylic groups (example 1) and fluorescein-labeled, it is possible to see using confocal microscopy the presence of the modified polysaccharide on the surface of the restorative material (FIG. 2). On the top left of this figure, the bare resin R2 scanned by means of confocal microscopy laser appears dark because it is non-autofluorescent. Moreover, the bare R2 resin (top left of FIG. 2), albeit treated with fluorescein like the one covered by chitosan modified with methacrylic groups (example 1), could not link to the fluorescein label. This confirmed that the bare R2 resin did not have any interaction with the fluorescein label and did not emitted any auto-fluorescence if excited by the confocal laser. On the right side of FIG. 2 a vertical cross-section of the R2 resin covered by the chitosan modified with methacrylic groups (example 1) and fluorescein-labeled could be observed. As previously described, the resin appears as a dark background whereas the fluorescein-labeled chitosan appears to be as a bright homogeneous and compact layer. It should be noted that the extensive washing of the sample with deionized water prior to testing allows excluding that the modified chitosan layer is anchored to the resin due to the presence of only weak interactions.

Figure 3:
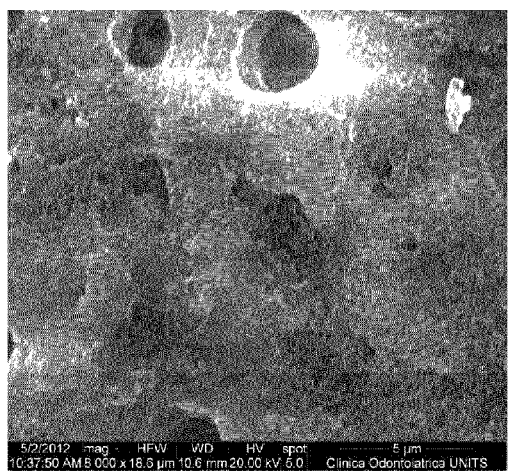
FIG. 3. Scanning Electronic Microscope (SEM) images of a dental element extracted and demineralized after exposure to an aqueous solution of chitosan modified with methacrylic acid prepared according to example 1. On the surface of the dental element, the polysaccharide chain aggregates of the modified chitosan are visible as a rough and disordered layer covering the dentin substrate.

Moreover, the ability of the chitosan modified with methacrylic groups to establish electrostatic interactions with the organic part of the demineralized dentin is demonstrated in FIG. 3. In this case, the modified chitosan prepared according to example 1 was put in contact with an extracted dental element. The latter was, then, washed extensively in order to remove the layer of chitosan not strongly anchored. The SEM analysis allows the identification of polysaccharide chains of the modified chitosan on the surface of the dental element. The scientific literature reports several SEM microscopies of acid etched dentin surfaces (Pashley D H et al. *Dent Mater* 2011; 27(1):1-16.) where the collagen substrate and the dentinal tubules could be clearly seen. In our case, FIG. 3, albeit the dentinal substrate was acid etched as the once reported in literature, the collagen dentinal substrate appears to be covered by a rough and disordered layer clearly referable to the modified chitosan. This result proves the existence of electrostatic interactions between the modified chitosan and the components of collagen and glycosaminoglycans exposed on the surface.

The modified chitosans were incorporated within an adhesive system as exemplified in example 5. The adhesive composition of example 5 includes the small monomer HEMA as many commercial "etch & rinse" adhesive systems contain HEMA, for example XP Bond® (Dentsplay De Tray, Konstanz, Germany), Peak LC Bond® (Ultradent, South Jordan, Utah, USA), Optibond Solo Plus® (Kerr, Orange, Kans., USA), iBond total Etch® (Heraeus Kulzer GmbH, Germany), Optibond FL® (Kerr, Orange, Kans., USA).

Preparation and Analysis of Samples

The adhesive compositions containing methacrylated chitosan prepared according to example 1 were tested in vitro using different tests to evaluate the bonding strength of the adhesive containing chitosan modified with acrylic groups. Extracted human dental elements were used. The latter were dissected using a microtome (Isomet 5000, Buhler) to obtain samples with a height of about 4 mm. The adhesion procedures were carried out on the dentin surface using as materials the experimental adhesive prepared as shown in example 5 (Group 1) and a control group (adhesive whose only difference is the absence in the composition of example 5 of the methacrylated chitosan; Group 2).

The samples are subjected to the following treatments:

1. Etching step: an etching agent containing 37% phosphoric acid was used;
2. Conditioning step: a conditioning agent containing methacrylated chitosan (Group 1) or without methacrylated chitosan (Group 2) was applied to the dentin surface and then dried using a mild air flow to evaporate the solvent;
3. Adhesive step: the adhesive resin R2 of example 9 was applied on the dentin surface, and then let to cure on mild air flow and light for 40 seconds using a LED lamp (Valo, Ultradent Product Inc. South Jordan, Utah, USA).

After the adhesive procedures (application of etchant, conditioner and adhesive), a commercial composite resin (Filtek Z250, 3M ESPE, Saint Paul, Minn., USA) was stratified in such a way as to simulate a dental restoration in order to assess the features of the new experimental adhesive composition, the samples were subjected to an aging treatment, which allowed reproducing the conditions inside the oral cavity. The two aging methods used were 1) dynamic thermo-mechanical, using a chewing simulator associated to a thermocycler; 2) static, with aging in artificial saliva inside an incubator at 37° C. for 24 hours.

The use of a thermo-mechanical chewing simulator is a very recent sample aging technique. The number of cases in the literature where this method has been taken into account is still limited (Steiner M et al., *Dent Mater,* 2009, 25, 494-499. Lutz F. et al., *J Dent Res,* 1992, 71, 1525-1529. Rosentritt M. et al., *J Dent Mater,* 2008, 36, 1048-1053. Rosentritt M. et al., *Dent Mater,* 2009, 25, 348-352. Rosentritt M. et al., *Dent Mater,* 2006, 22, 176-182). In an article of 2011, Mayoral et al. (Mayoral J. R. et al., *Clin Oral Investig,* 2011, 15, 257-264) evaluated the variation of the marginal adaptation of dental restorations when subjected to mechanical and thermal stresses. The final results showed an overall reduction of the marginal adaptation as a result of the chewing simulation and thermo-cycling, in both classes of cavities analyzed and for all the adhesive systems applied.

Figure 7:
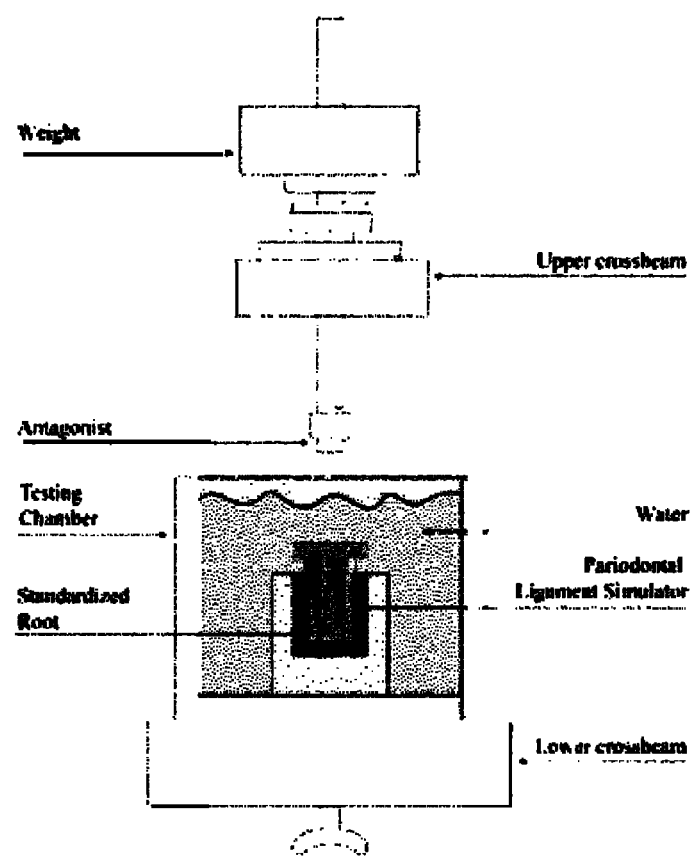
FIG. 7. Diagram of the thermo-mechanical chewing simulator.

The thermo-mechanical aging treatment used herein provided for the use of the CS-4.4 (SD Mechatronik GmbH, Germany) Chewing Simulator (CS) associated with a thermal cycler (FIG. 7). The samples subjected to thermo-mechanical treatment were partially immersed in a temporary restorative material Protemp 4 (Temporization Material, lot: C 434261, exp. date: 2014-05, 3 m ESPE) cast in a polytetrafluoroethylene (PTFE) mold (15 mm diameter). In order to ensure a perfect parallelism between the composite material and the Chewing Simulator antagonist, the samples were compressed with the same CS very cautiously inside the mold filled with Protemp 4. This process made it possible to obtain all the samples with a "standard root". Further attention was paid to the simulation of the periodontic ligament. This element was obtained by immersing the "standard root" in an impression material Even Express 2 (Impression Material, lot: F 546236, exp. date: 2014-06, 3M ESPE). The elastic properties of the impression material were used to simulate the elasticity of the periodontic ligament.

In order to simulate 5 years of clinical service in the oral cavity, the samples were subjected to the thermo-mechanical aging treatment in which a compressive force of 50 N value with a frequency of 1 Hz stressed the samples for a time equal to 15 days (equivalent to $1.2 \times 10^6$ cycles). At the same time, the samples were thermally stressed by alternating the immersion in demineralized water at temperatures of 5° C. and 55° C. The thermal cycle provided for a retention time of 60 s at the two different temperatures. In total there were 6,000 thermal cycles.

Afterwards, the samples were dissected with the microtome to obtain samples sized 0.9×0.9×8.0 mm. Each of them was subjected to the microtensile test using the non-trimming technique (Armstrong, S. et al., *Dental Mater,* 2010, 26, e50-62) and each sample was brought to fracture using a speed of 0.5-1.0 mm/min (Bisco Inc.; Schaumburg, Ill., USA) to evaluate the bonding strength of the adhesive system. The values recorded in Newton (N) were later transformed in the Stress unit (MPa) and analyzed using the ANOVA statistical test. The values were statistically significant with a $p<0.05$. As can be seen in Table 1, even if the bonding strength values are essentially identical between the two Groups examined after incubation in artificial saliva for 24 hours, as a result of aging with the thermo-mechanical chewing simulator, the sample of Group 1, i.e. that containing the methacrylated chitosan in the adhesive system, shows a bonding strength value greater than that of the control (Group 2) without addition of the modified polysaccharide. In particular, significant differences were found between Group 1 and Group 2 when subjected to mechanical chewing simulation associated with thermo-cycling ($T_{CS}$): Group 1 ($28.4\pm8.8^{aA}*$) and Group 2 ($18.0\pm6.0^{bB}*$). No statistically significant difference was observed when the groups were subjected to static aging in artificial saliva ($T_O$): Group 1 ($26.0\pm8.7^{aA}*$) and Group 2 ($25.5\pm8.7^{aA}*$).

It also noted that in Group 1, the bonding strength value of the restoration on the dental element remains substantially unchanged after a simulated aging process of 5 years.

TABLE 1

| | Microtensile test (MPa) at time zero ($T_0$, 24 hours in artificial saliva) and after chewing simulation/thermo-cycling ($T_{CS}$, $1.2 \times 10^6$ mechanical cycles + $66 \times 10^3$ heating cycles) (mean ± stand. dev.) | |
|---|---|---|
| | Aging time | |
| Adhesive system | $T_{CS}$ | $T_0$ |
| Group 1 | 28.4 ± 8.8$^{aA*}$ | 26.0 ± 8.7$^{aA*}$ |
| Group 2 | 18.0 ± 6.0$^{bB*}$ | 25.5 ± 8.7$^{aA*}$ |

*Different lower-case superscript letters indicate a statistical difference in the column and upper-case superscript letters indicate a statistical difference in the rows (p < 0.05).

Figure 4:
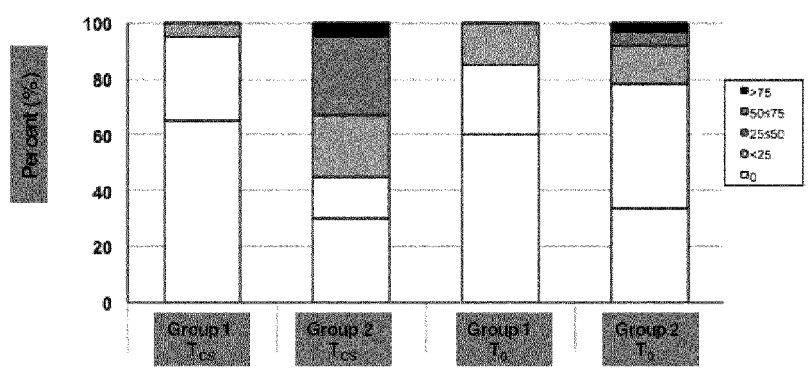
FIG. 4. The graph shows the distribution of silver nitrate ($AgNO_3$) at the level of the adhesive interface in the analyzed samples. The gray scale indicates the different degree of penetration of nanoparticles (nanoleakage) (0% to >75% value of infiltration of the adhesive) analyzed with a 100× magnification optical microscope.
Figure 5:
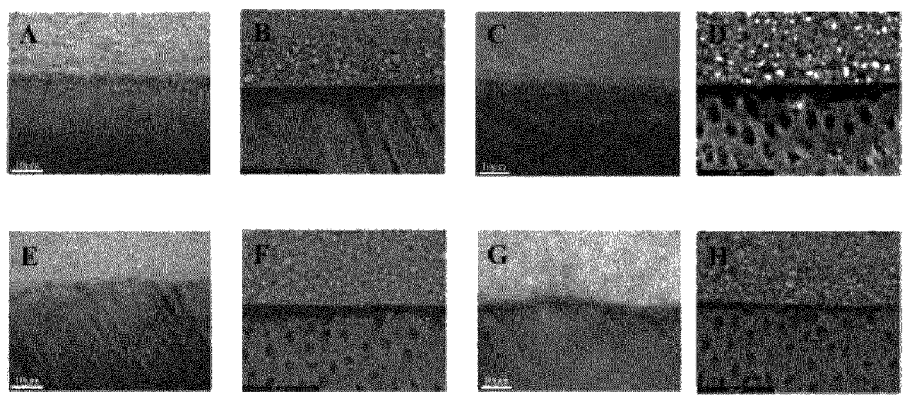
FIG. 5. The figure shows the set of significant images collected to analyze the nanoleakage of both groups tested, which were observed by using the optical microscope with 100× magnification: images A and C=Group 1, respectively $T_{CS}$ and $T_0$; images E and G=Group 2, respectively $T_{CS}$ and $T_0$. The samples were also observed with Scanning Electron Microscope (SEM): images B and D=Group 1, respectively $T_{CS}$ and $T_0$; images F and H=Group 2, respectively $T_{CS}$ and $T_0$.

Other samples, prepared in the same way as the microtensile test, were used to analyze the expression of nanoleakage at the hybrid layer level. The samples after the aging phase were dissected perpendicularly to obtain sections with a thickness of less than one millimeter. The samples were immersed in a solution of silver nitrate ($AgNO_3$) for 24 hours, and then washed, placed in a photo-developing liquid for 8 hours, and then polished using abrasive papers (Tay F. R. et al., *J Dent Res,* 2003, 82, 537-541). The samples were observed with a 100× magnification optical microscope (Leica D M R; Leica Wetzlar, Germany) and with a scanning electron microscope (Quanta 250; FEI, Hillsboro, Oreg., USA). The quantitative assessment of the presence of silver nitrate at the adhesive interface was carried out by two operators using the Saboia et al. method (Saboia V. P. A. et al., *Eur J Oral Sci* 2009, 117, 618-624). In FIG. 4 it can be seen that Group 2 (control) shows a significant increase of nanoleakage at the adhesive interface compared to Group 1, i.e. the samples treated with the adhesive system containing chitosan modified with acrylic groups both after dynamic aging ($T_{CS}$) and after static aging ($T_0$). Again, this result emphasizes the positive effect of the modified chitosan of the present invention in increasing the average duration of the dental restoration. This is also demonstrated by the results shown in FIG. 5 and obtained through analysis of the samples with the optical microscope and with the scanning electron microscope.

Figure 6:
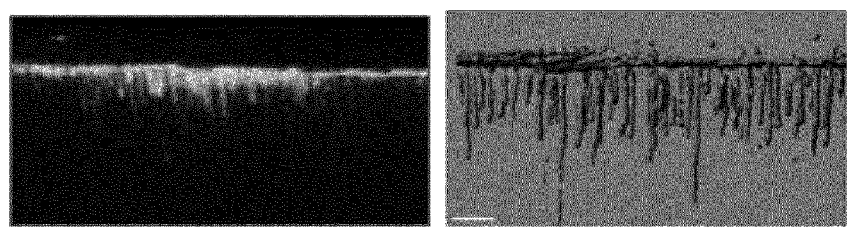
FIG. 6. The images were obtained using the fluorescence microscope on a dental restoration wherein chitosan-modified with acrylic groups (as per example 1)—labelled with fluorescein units was used. The samples show the presence of the modified chitosan of example 1 at the level of the adhesive interface and within the dentin tubules after the adhesion procedures.

In order to evaluate the permanence of chitosan in the adhesive interface, after the application of the adhesive systems, a fluorophore (fluorescein) was bound to the biopolymer in such a way as to make the chitosan visible when observed under a fluorescence microscope. The samples were prepared following the same method used for the nanoleakage analysis. As can be seen in FIG. 6, after static aging in artificial saliva for 24 hours, the methacrylated chitosan is still present, indicating its firm anchoring to the interface between the demineralized tooth and the restorative material.

The invention claimed is:

1. A chitosan modified by derivatization of residues —$NH_2$ of D-Glucosamine units represented by the general formula I

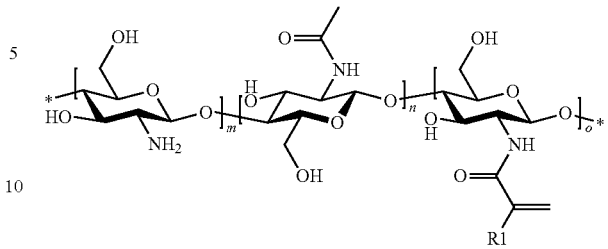

wherein:
the chitosan has a degree of total substitution with CO—C($CH_2$)$R_1$ acrylic and acetyl residues of the —$NH_2$ residues of D-Glucosamine units comprised from 10% to 50% with a ratio between acrylic and acetyl residues comprised from 0.1 to 9; and
$R_1$ is selected from H, a halogen, a linear or branched $C_1$-$C_3$ alkyl chain, optionally substituted with an OH or a halogen, and $NHCOR_2$ with $R_2$ equal to a linear or branched $C_1$-$C_3$ alkyl chain.

2. The chitosan modified by derivatization of —$NH_2$ residues of D-Glucosamine units according to claim 1, wherein the chitosan has a degree of residual acetylation comprised from 5 to 20%.

3. The chitosan modified by derivatization of —$NH_2$ residues of D-Glucosamine units according to claim 1, wherein the degree of substitution with acrylic residues comprised from 5 to 24%.

4. The chitosan modified by derivatization of —NH2 residues of D-Glucosamine units according to claim 1, wherein the ratio between acrylic and acetyl residues is 1:1.

5. The chitosan modified by derivatization of —$NH_2$ residues of D-Glucosamine units according to claim 1, wherein the chitosan has a molecular weight lower than 400,000 Da and higher than 20,000 Da.

6. The chitosan modified by derivatization of —$NH_2$ residues of D-Glucosamine units according to claim 5, wherein the chitosan has a molecular weight comprised from 20,000 Da to 300,000 Da.

7. The chitosan modified by derivatization of —$NH_2$ residues of D-Glucosamine units according to claim 1, wherein $R_1$ is selected from H, $CH_3$, $CH_2CH_3$, $CH_2CH_2CH_3$, $CH_2CH_2OH$, Br, $CH_2Br$ and $NHCOCH_3$.

8. A composition with adhesive properties comprising at least one chitosan modified by derivatization of —$NH_2$ residues of D-Glucosamine units as defined in claim 1.

9. The composition with adhesive properties according to claim 8, wherein the chitosan modified by derivatization of —$NH_2$ residues of D-Glucosamine units is comprised in an amount equal or lower than 4% w/V.

10. The composition with adhesive properties according to claim 9, wherein the chitosan modified by derivatization of —$NH_2$ residues of D-Glucosamine units is comprised in an amount comprised from 0.2 to 2% w/V.

11. The composition with adhesive properties according to claim 8, wherein an acrylic compound in an amount equal or higher than 10% (V/V) and water in an amount equal or higher than 30% (V/V) are further comprised.

12. The composition with adhesive properties according to claim 11, wherein the water is in an amount comprised from 40% to 50% (V/V).

13. The composition with adhesive properties according to claim 11, wherein the acrylic compound is in an amount comprised from 10% to 30% (V/V).

14. The composition with adhesive properties according to claim 11, wherein the water solution has a pH value comprised from 1 to 6.5.

15. The composition with adhesive properties according to claim 14, wherein the pH value is 5.5.

16. A method for preparing an adhesive system for use in a dental, orthopedic, or ophthalmic treatment, the method comprising the steps of:

(a) providing a chitosan modified by derivatization of residues —$NH_2$ of D-Glucosamine units represented by the general formula I

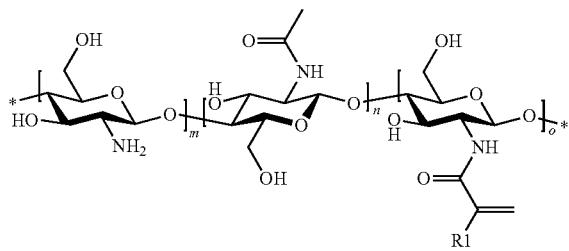

wherein:
the chitosan has a degree of total substitution with CO—C($CH_2$)$R_1$ acrylic and acetyl residues of the —$NH_2$ residues of D-Glucosamine units comprised from 10% to 50% with a ratio between acrylic and acetyl residues comprised from 0.1 to 9; and
$R_1$ is selected from H, a halogen, a linear or branched $C_1$-$C_3$ alkyl chain, optionally substituted with an OH or a halogen, and $NHCOR_2$ with $R_2$ equal to a linear or branched $C_1$-$C_3$ alkyl chain;
(b) combining the chitosan of step (a) with appropriate additives or excipients for use in a dental, orthopedic, or ophthalmic treatment.

* * * * *